(12) United States Patent
Dewey et al.

(10) Patent No.: US 9,585,638 B2
(45) Date of Patent: Mar. 7, 2017

(54) SYSTEM FOR CLASSIFYING PALPABLE SOFT TISSUE MASSES USING A-MODE ECHOGRAPHS

(71) Applicants: Russell Dewey, Los Altos, CA (US); Kenneth Purfey, San Jose, CA (US); Kenneth Jacobsen, Fremont, CA (US)

(72) Inventors: Russell Dewey, Los Altos, CA (US); Kenneth Purfey, San Jose, CA (US); Kenneth Jacobsen, Fremont, CA (US)

(*) Notice: Subject to any disclaimer, the term of this patent is extended or adjusted under 35 U.S.C. 154(b) by 331 days.

(21) Appl. No.: 13/903,886

(22) Filed: May 28, 2013

(65) Prior Publication Data

US 2014/0039311 A1 Feb. 6, 2014

Related U.S. Application Data

(63) Continuation-in-part of application No. 12/718,969, filed on Mar. 6, 2010, now abandoned.

(51) Int. Cl.
*A61B 8/08* (2006.01)
*A61B 8/00* (2006.01)

(52) U.S. Cl.
CPC .......... *A61B 8/5223* (2013.01); *A61B 8/085* (2013.01); *A61B 8/0825* (2013.01); *A61B 8/4483* (2013.01); *A61B 8/5207* (2013.01); *A61B 8/42* (2013.01); *A61B 8/4455* (2013.01); *A61B 8/461* (2013.01)

(58) Field of Classification Search
None
See application file for complete search history.

(56) References Cited

U.S. PATENT DOCUMENTS

| | | | |
|---|---|---|---|
| 4,467,653 A | 8/1984 | Turbe | |
| 4,511,984 A | 4/1985 | Sumino et al. | |
| 4,779,623 A | 10/1988 | Sumino et al. | |
| 5,078,148 A | 1/1992 | Nassi et al. | |
| 5,090,413 A | 2/1992 | Yoshioka | |
| 5,099,848 A * | 3/1992 | Parker et al. | 600/443 |
| 5,361,767 A | 11/1994 | Yukov | |
| 5,613,493 A | 3/1997 | Schafer | |
| 5,720,286 A | 2/1998 | Chapelon et al. | |
| 6,012,332 A | 1/2000 | Schafer | |
| 6,106,464 A | 8/2000 | Bass et al. | |
| 6,500,119 B1 | 12/2002 | West et al. | |
| 6,554,774 B1 | 4/2003 | Miele | |
| 6,875,176 B2 | 4/2005 | Mourad et al. | |

(Continued)

OTHER PUBLICATIONS

"Application of Echo-Ranging Technique to the Determination of Structure of Biological Tissue", Journal of Science, Feb. 29, 1952, vol. 115, No. 2983, pp. 226-230.

*Primary Examiner* — Serkan Akar
(74) *Attorney, Agent, or Firm* — Maryam Imam; IPxLaw Group LLP

(57) ABSTRACT

A system comprising an A-mode ultrasonic apparatus and a data processing apparatus and a stored program method is disclosed, for classifying a palpable breast mass based on analyzing data from a digital a-mode ultrasound Echograph of the observed mass and communicating the results of that classification directly to a user of the system in the form of a simple color-coded text block depending on whether the system determines the observed breast mass to be more-likely abnormal or more-likely not abnormal.

4 Claims, 6 Drawing Sheets

(56) References Cited

U.S. PATENT DOCUMENTS

| | | |
|---|---|---|
| 7,022,077 B2 | 4/2006 | Mourad et al. |
| 7,033,321 B1 | 4/2006 | Sarvazyan |
| 7,048,691 B2 | 5/2006 | Miele et al. |
| 7,397,323 B2 | 7/2008 | Tavassoli Hozouri |
| 7,455,406 B2 | 11/2008 | Miwa et al. |
| 7,503,896 B2 | 3/2009 | Miele et al. |
| 7,815,574 B2 | 10/2010 | Mourad et al. |
| 8,133,181 B2 | 3/2012 | Yuk et al. |
| 8,147,410 B2 | 4/2012 | Zheng |

* cited by examiner

SYSTEM FOR CLASSIFYING PALPABLE SOFT TISSUE MASSES USING A-MODE ECHOGRAPHS

CROSS REFERENCE TO RELATED APPLICATIONS

This application is a continuation-in-part of U.S. patent application Ser. No. 12/718,969, filed on Mar. 6, 2010, by Russell H. Dewey, et al., and entitled "MOBILE ULTRASOUND SYSTEM WITH COMPUTER-AIDED DETECTION", which is incorporated herein by reference as though set forth in full.

BACKGROUND

Field of Invention

The presently disclosed invention relates generally to medical device detection devices and more particularly to ultrasound devices with detection capability.

Description of Prior Art

A-mode ultrasound is the simplest mode of ultrasound pulse-echo technology having a single pulse-echo element that produces a one-dimensional data vector consisting of the amplitude of the ultrasonic echo sampled at regular time intervals since the time of the pulse.

An A-mode Echograph (also known as an echogram, or time-amplitude graph) is a Cartesian graph in which the horizontal axis represents the time (t) required for the return of the echo from an ultrasound pulse, and the vertical axis (a) represents the strength or amplitude of the echo at each value of t. The greater the reflection at the tissue interface, the larger the signal amplitude.

One of the earliest applications of A-mode Echographs in medical diagnostics was for the evaluation of breast tumors. Prior art breast cancer detection systems using A-mode ultrasound Echographs are well known. In these systems, the ultrasound echo waveforms of living intact breast tumors are displayed as Echographs on an analog oscilloscope.

Further, a quantitative index has been developed by prior art technology for breast tumor comparison, called the A-scan area ratio, also referred to as the A-mode area ratio, which was introduced for the purpose of classifying soft tissue abnormalities. The A-mode area ratio was originally calculated by comparing the area subtended under an analog A-mode time-amplitude Echograph to a base line area value and computing the ratio. If the A-mode area ratio ratio is greater than 1.0, the soft tissue abnormality is likely abnormal. If the ratio is less than 1.0, the soft tissue abnormality is likely non-abnormal. To summarize, an abnormal breast mass has greater echogenic density.

However, the A-mode type of diagnostic ultrasound has been long abandoned and replaced with B-mode ultrasound technology. Today the field of ultrasound diagnostics is clearly dominated by work on B-mode, C-mode, M-mode, Doppler mode, and others.

All prior art techniques however, suffer from inaccuracies because they use manual and/or analog methods that are not suitably accurate or reliable.

Therefore, what is needed is a method and apparatus for the classification and detection of palpable soft tissue masses, such as breast mass(es).

Prior art methods for classification of breast masses using A mode probes used an analog oscilloscope for its output and directly displayed raw echo wave forms which then need to be interpreted by trained personnel.

Further, in prior art techniques for classification of breast masses using A mode probes used human doctors to process the observed data, measure areas subtended by displayed analog waveforms, and draw an inference therefrom.

The inference method used by prior art for classification of breast masses is a manual calculation of the A mode area ratio method using visual inspection of the displayed analog ultrasound data. The accuracy of the prior art A mode area ratio method is flawed in the two following ways. First, it includes within the computed total area beneath the waveform that represents echoes from the breast skin where the probe is placed as well as including the area beneath the waveform that represents echoes from the breast mass itself. Second, the method of computation involves visual inspection and estimation of wave traces on a small screen oscilloscope with a limited amount of data available.

Additionally, the referenced prior art apparatus for the classification of breast masses using A-mode probes uses a custom analog A-mode ultrasound probe to acquire the observed data.

Prior art apparatus for the classification of breast masses using A-mode probes uses an analog oscilloscope for its output means, directly displaying raw echo wave forms which then needed to be interpreted by trained personnel.

IN THE DRAWINGS

SUMMARY OF THE INVENTION

Figure 1:
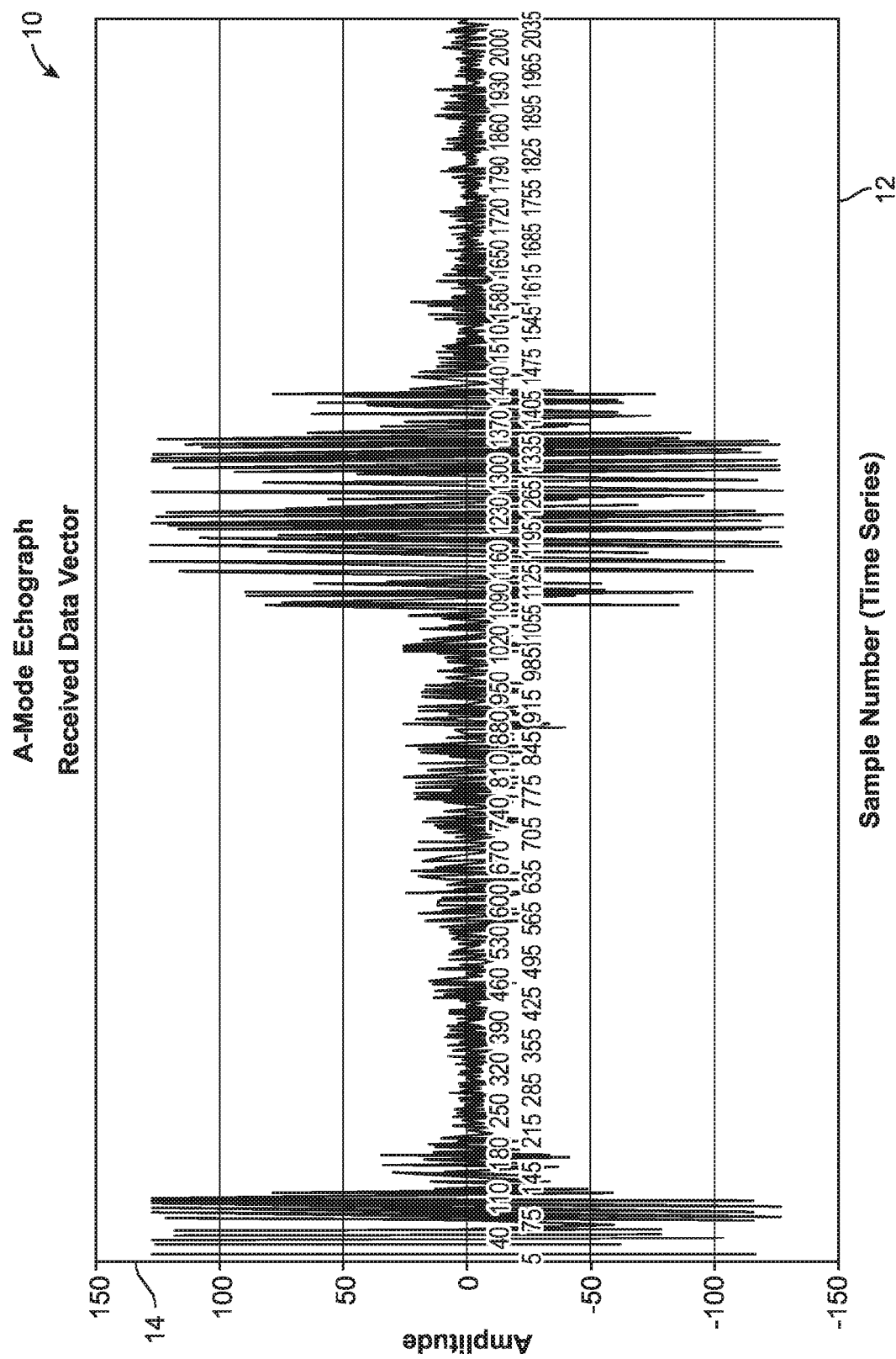
FIG. 1 illustrates an Echograph 10 of the contents of an actual data vector as received by the data processing methods of the invention.

Briefly, a system for classifying palpable breast masses using digital a-mode Echographs is disclosed. In accordance with an embodiment of the invention, a system includes an A-mode ultrasonic apparatus and a data processing apparatus and a stored program method is disclosed, for classifying a palpable breast mass based on analyzing data from a digital a-mode ultrasound Echograph of the observed mass and communicating the results of that classification directly to a user of the system in the form of a simple color-coded text block depending on whether the system determines the observed breast mass to be more-likely abnormal or more-likely not abnormal.

These and other objects and advantages of the present invention will no doubt become apparent to those skilled in the art after having read the following detailed description of the preferred embodiments illustrated in the several figures of the drawing.

DETAILED DESCRIPTION OF THE VARIOUS EMBODIMENTS OF THE INVENTION

An embodiment of the invention utilizes a color-coded rectangle shape with overlaid text displayed on a pixel-based display screen whereby the color code communicates the output results indicating whether an observed soft tissue mass, such as a breast mass, is either likely abnormal or likely non-abnormal. This advantageously eliminates the need for trained personnel and allows a layperson ready access to detection. In an embodiment of the invention, the results are displayed using commercially available digital data processing apparatus, such as a personal computer or a smartphone. Thus the inference performed on observation data is faster, more accurate, more consistent, and more repeatable.

In various embodiments of the invention, flaws due to extraneous counting of areas resulting from epidermal echos not related to the soft tissue mass being observed are eliminated, and by automating the A-mode area ratio method through a stored program method within the data processing apparatus operating on digital data representing frequently sampled values of the amplitude variable.

Further, utilization of consumer-grade commercial sources is cost effective thus placing the system within affordable reach of millions of consumers worldwide.

The following summarizes the names and reference numbers for some of the relevant components of the various embodiments of the invention.

- 100 A digital single-element (A-mode) ultrasound probe
- 101 An A-mode ultrasonic transducer (within 100)
- 102 A clock-based means for sampling analog echos and converting the samples into vectors of digital amplitude values
- 104 A digital observation vector comprised of digital amplitude values from one sampled echo, from one ultrasound observation
- 106 A transmitting means for transmitting an observation data vector to a receiving means
- 200 A data processing apparatus for processing digital observation vectors
- 210 A LIFO buffer for storing received data vectors
- 220 A stored program within the data processing apparatus for processing received data vectors, for creating a an internal digital Echograph as an array of numeric amplitude values versus sample time since the time of the originating ultrasound pulse, and for classifying soft tissue mass(es), such as breast masses, from those Echographs
- 230 A baseline control value used for comparing the area subtended beneath an Echograph of an observed soft tissue mass(es), such as breast masses, to the area subtended beneath the Echograph of a typical benign mass
- 240 A results means, comprising a pixel-based display, for communicating the resulting breast mass classification directly to the system user, in the form of a simple colored shape with overlaid text.
- 250 A looping means to retrieve the next available input data vector for processing.

A system comprising an A-mode ultrasonic apparatus and method is disclosed for classifying palpable soft tissue mass(es), such as breast masses, based on analyzing data from an A-mode ultrasound Echograph of the mass and then communicating the results of that classification directly to a user of the system in the form of a simple (first) color, such as yellow or a second color, such as green, text block depending on whether the system determines the observed soft tissue mass to be more-likely abnormal or more-likely non-abnormal.

Referring now to FIG. 1, an Echograph 10 illustrates the contents of an actual data vector as received by the data processing methods of the invention. With respect to the graph of FIG. 1, the vertical axis 14 shows the value of the amplitude of the reflected ultrasound signal, and typically ranges between some maximum negative number and some maximum positive number, depending on the sampling board in the ultrasound probe. The horizontal axis 12 shows the time, in equal increments, since the time of the pulse. The ultrasound probe, shown and discussed relative to subsequent figures, samples the echo form the pulse at each of the time intervals at the axis 12 until the next pulse is sent. The number of timed samples of each echo is a design choice, typically determined by the manufacturer of the probe. In FIG. 1, the total distance of travel of the ultrasound signal is approximately 5 centimeters (cm) in total depth from the surface of the skin. The large echo, shown at the extreme left of the Echograph 10 is the epidermal echo from ultrasound signals passing through the skin of the soft tissue. Notably, the large echo that begins at approximately 2.5 cm below the surface of the skin and is approximately 1 cm thick is the observation echo from a palpable soft tissue mass.

Figure 2:
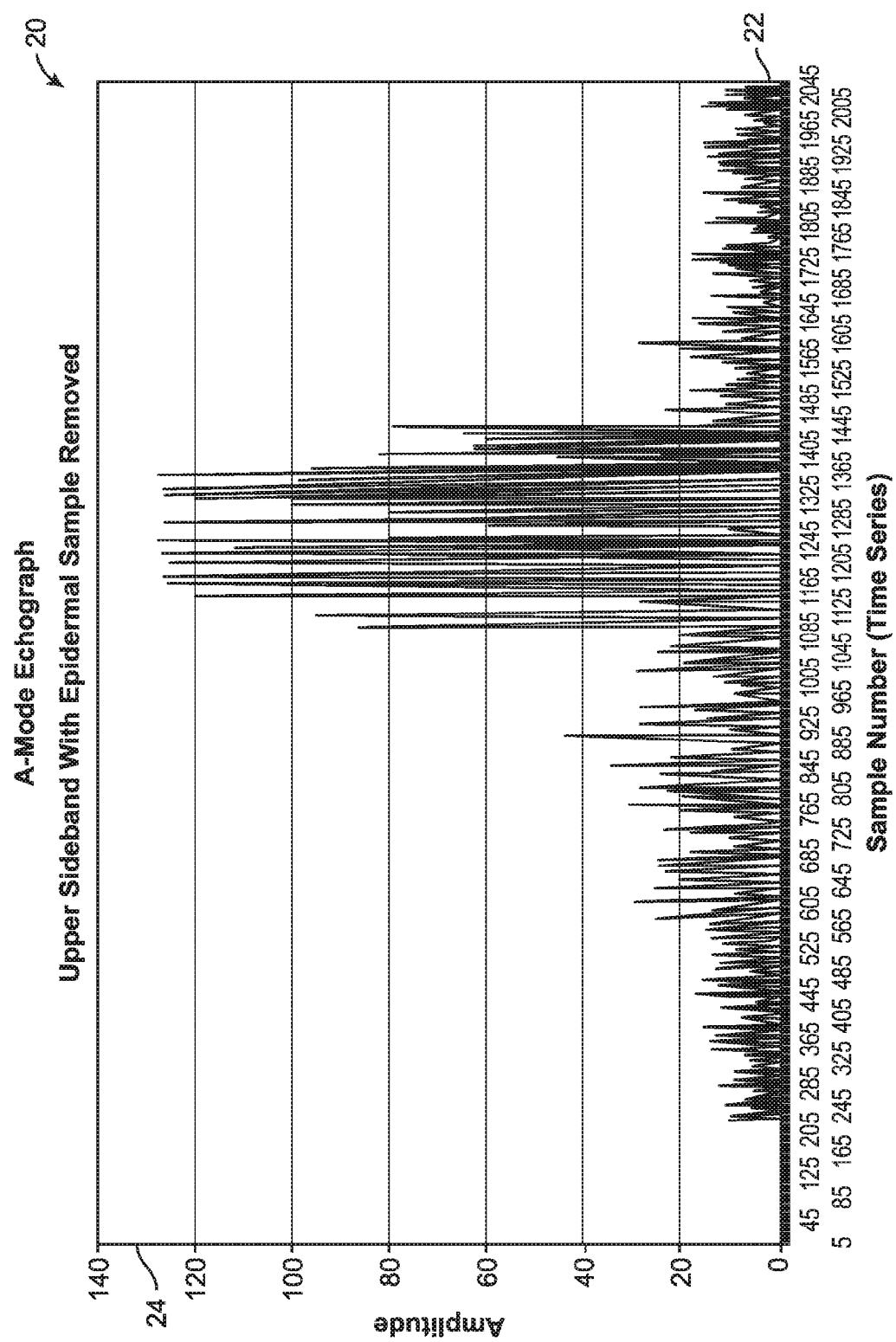
FIG. 2 shows the Echograph 20 from FIG. 1 after converting it to single side band form and after removing the unwanted data from epidermal echos.

FIG. 2 shows the Echograph 20 from FIG. 1 after converting it to single side band form and after removing the unwanted data from epidermal echos. The horizontal axis 22 show sample numbers (in time series) and the vertical axis 24 shows amplitude. For the method presently disclosed, only the upper side band is required. In addition, various methods of the invention are used to measure the ecogenic density of soft tissue masses, and not that of the user's skin—which typically vary by gender, age, and ethnicity. The first N data samples are simply thrown out, with the value of N determined by manual inspection of a sample of Echographs produced using the same ultrasonic apparatus, and then stored as a global constant in the exemplary methods of the invention.

Figure 3:
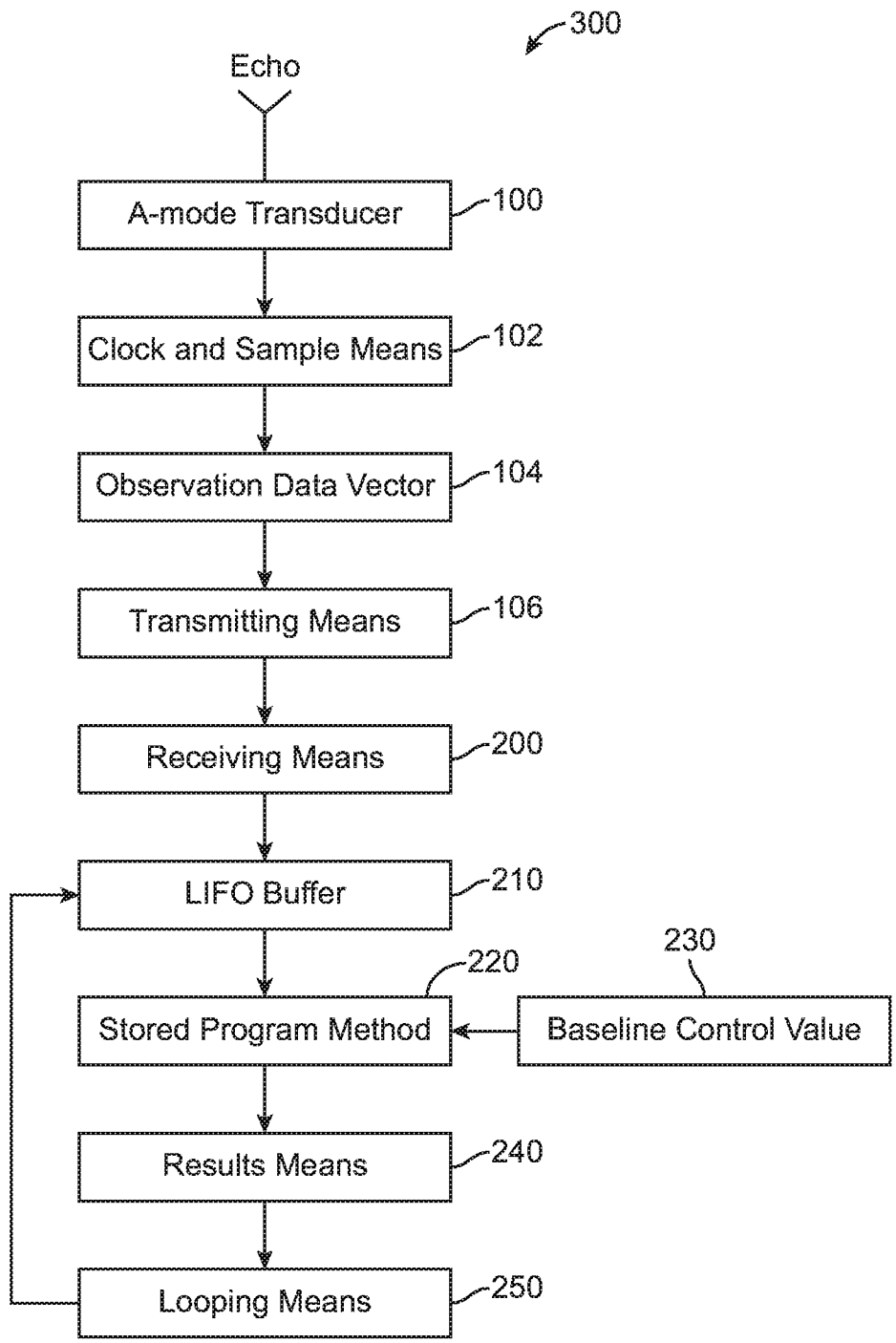
FIG. 3 shows a flow chart 300 of the relevant steps performed when an A-mode ultrasonic echo is received and then processed by the various embodiments of the invention.

FIG. 3 shows a flow chart 300 of the relevant steps performed when an A-mode ultrasonic echo is received and then processed by the various embodiments of the invention. At step 100, an A-mode transducer transmits a signal that is sampled at a particular clock rate at step 102. Next, observation data vector is generated from the sampled data of step 102. At step 106, the vector of step 104 is transmitted and at step 200, the transmitted data of step 106 is received. Next, at step 210, a last-in-first-out (LIFO) buffer stores the received data and the stored data is stored at step 220. A baseline control value is derived at step 230. At step 240, results are generated and the process goes back to and repeats from the step 210. More specifically, at step 102, a time-based sampling means, including a clock, samples each received analog echo a plurality of times and creates a digital observation data vector, the data vector of step 104, which is comprised of a one-dimensional array of numerical values describing the timed life-cycle of said echo as an amplitude-time graph. The transmitting means of step 106 transmits the observation data vector to a receiving means, the LIFO buffer of step 201, within a data processing apparatus of step 200.

Figure 4:
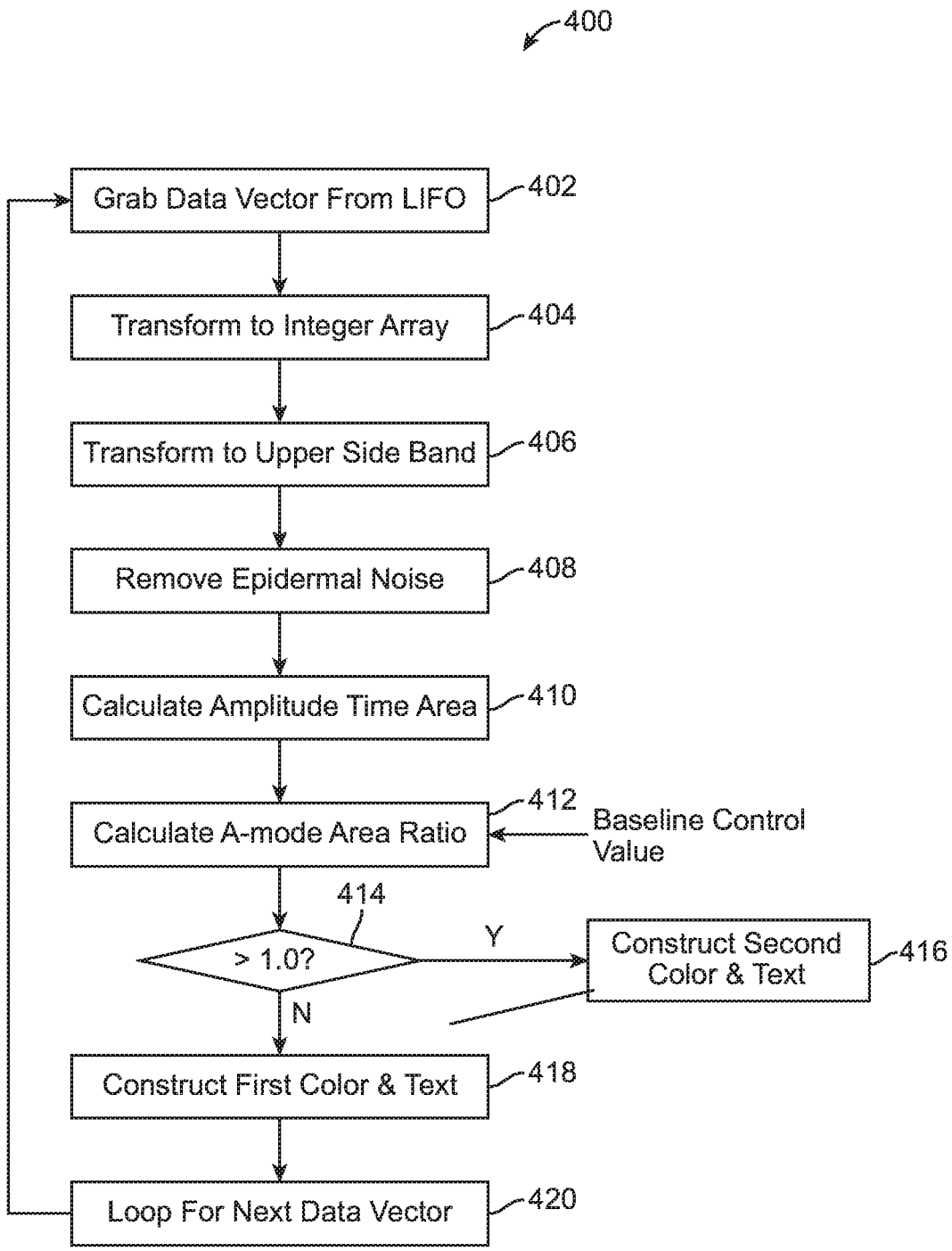
FIG. 4 shows a flow chart 400 of an embodiment of the invention for storing program method (at step 220 of FIG. 3).

FIG. 4 shows a flow chart 400 of an embodiment of the invention for storing program method (at step 220 of FIG. 3).The following steps are shown being performed in FIG. 4, in accordance with a method of the invention Step 402 Getting the most recently arrived data vector from the last-in-first-out LIFO buffer, Step 404 Transforming the input data vector from Step 402, if necessary, so that it is in the form of a one-dimensional array of integer values ranging from some maximum negative amplitude value to some maximum positive amplitude value, Step 406 Transforming the input data vector from Step 404, if necessary, keeping only the upper side band, so that only zero and positive integer values remain. The easiest way to do this is to take the replace each data vector value with the absolute value of that data vector value, Step 408 Removing unwanted echo amplitude data corresponding to those echos known to result from the ultrasound energy passing through the epidermal layer of a user's body. This data should not enter into the area calculations for soft tissue (such as breast tissue) only. The easiest way to do this is to replace each of the first N data vector values with the integer 0 (zero).

Step 410 Calculating the amplitude-time area of the remaining sampled amplitude values. Unlike the prior art in which analog data was used for this calculation, the present invention must perform the calculation on digital samples taken from the original wave form. Thus the area must be approximated by other methods. The easiest approximation (although with a small error) is to simply sum together all of the individual digital amplitude values from all of the timed samples of this echo remaining after step 408

Step 412 Calculating the A-mode area ratio by dividing the area approximated in step 410 by a control area value representing an average area for non-abnormal masses. The control value needs to be determined only once by sampling and measuring the area beneath a number of Echographs of known non-abnormal masses and then storing the control area value as a global constant in this stored program method.

Step 414 Deciding on whether the observed mass is likely abnormal or likely non-abnormal, using the following logic: if the A-scan area ratio from Step 412 is greater than 1.0, the observed mass is considered to be likely abnormal, otherwise, the observed mass is considered to be likely non-abnormal.

Steps 416 and 418 Showing the result of Step 7 to the system user, using the following logic: if the mass is likely abnormal, paint a result text box on a display means with a solid yellow color and overlay the colored text box with words to the effect that the mass observed is most-likely abnormal and the user should have it checked by a physician. Otherwise, paint a result text box on a display means with a solid green color and overlay the colored text box with words to the effect that the mass observed is most likely non-abnormal, but it is always a good practice for the user to have regular examinations with her/his physician.

Step 420 Looping back to Step 402 and grabbing the next data vector for processing.

Figure 5:
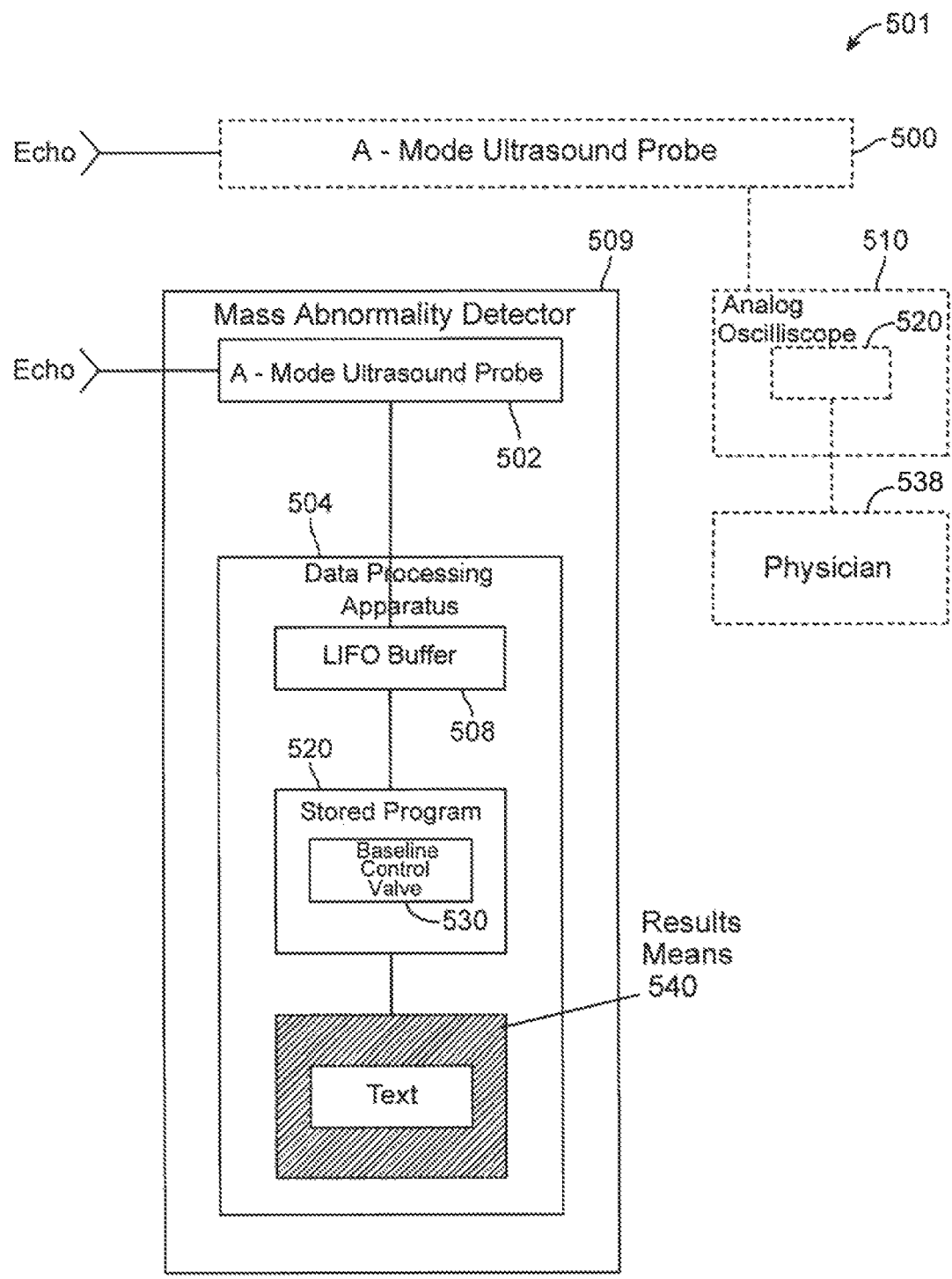
FIG. 5 shows a block diagram of a mass abnormality detection system 501, in accordance with an embodiment of the invention.

FIG. 5 shows a block diagram of a mass abnormality detection system 501, in accordance with an embodiment of the invention. The system 501 is shown to include an analog single-element (A-mode) ultrasound probe 500, an analog oscilloscope 510, a trained human physician 538, and a mass abnormality detector 509, in accordance with an embodiment of the invention. The oscilloscope 510 is shown to include an analog Echograph that is shown to be used by the physician 538. The detector 509 is shown to include a digital single-element (A-mode) ultrasound probe 502 and a data processing apparatus 504. The data processing apparatus 504 is shown to include a LIFO buffer 508, a stored program 520, and a results means 540. The stored program 520 is shown to include a baseline control value 530.

The oscilloscope 510 is shown coupled to the probe 500. The probe 502 is shown coupled to the LIFO buffer 508, which is shown coupled to the stored program 520, which is shown coupled to the results means 540. It is understood that the stored program 520 is executed by a processor well known in the art. The functions of the structures of the system 501 include the following:

The last-in-first-out LIFO buffer 508 stores received data vectors until a method executing in the data processing device is available to process the most recently arrived data vector. This buffer is required because the ultrasound probe 502 may be sending data vectors to the data processing apparatus 504 at a different rate than the stored program can handle. The stored program 520, when executed, causes processing of the input data vectors and classifying the observed palpable soft tissue mass, which classification is an inference drawn from said observation vector. The baseline control value 530 represents a threshold amplitude-time value for classifying an observed soft tissue mass as either normal or non-normal. The results means 540 causes communication of the results of the classification determined by the stored program method 520 directly to a system user. In an embodiment of the invention, this communication is in the form of a simple colored shape with overlaid text. The step of the looping means, in FIG. 3 causes looping back to the LIFO buffer 210 and grab the next most recent vector for processing. The probe 500, in an embodiment of the invention, is an analog single-element (A-mode) ultrasound probe. The analog oscilloscope 520 displays an analog Echograph 528, also called a waveform, of received RF signal amplitude of the ultrasound echo from a palpable soft tissue mass, versus time since the corresponding pulse of the probe. The area under the waveform 528 is called the A-Mode area. The physician 538 who visually inspects the waveform on the oscilloscope, manually calculates the area under the wave form, and compares the area from the observed soft tissue mass to a baseline of areas calculated from known benign masses. The physician 538 then makes a determination as to whether the observed mass was likely benign or likely malignant.

Figure 6:
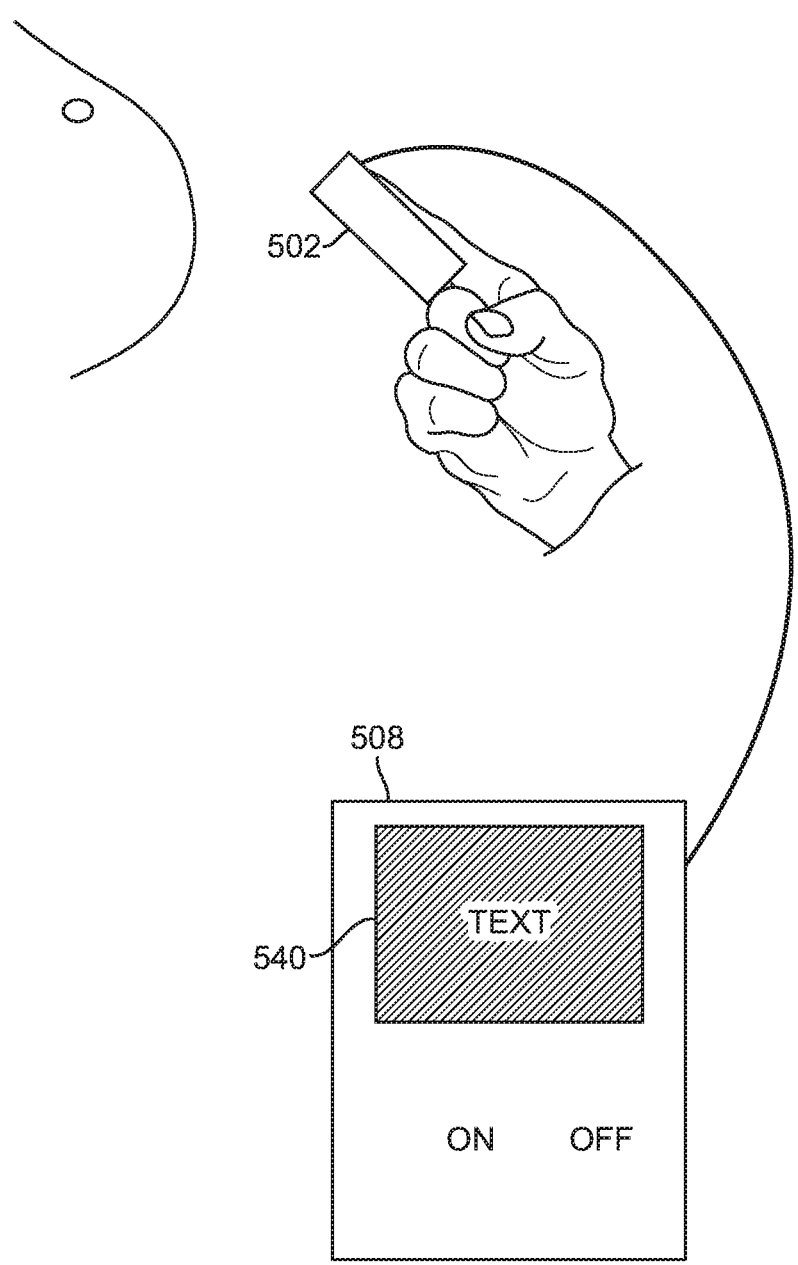
FIG. 6 illustrates an application of an exemplary embodiment of the invention.

FIG. 6 illustrates an application of an exemplary embodiment of the invention.

(1) First, the user turns on, or powers up, the system. Upon power up, the result display screen will show a default initial state comprising a solid green color with overlaid text.

(2) Next, a user of the system positions the tip of the system's A-mode ultrasound probe at the location on the user's soft tissue where the user (or the user's physician) has previously detected a palpable soft tissue mass.

(3) The display screen 240 on the data processing device 200 will immediately turn yellow if the system method 220 determines that the observed mass is likely abnormal, or else the display screen will continue to show solid green—meaning nothing abnormal has been detected so far.

Accordingly, the reader will see that the results achieved by the invention are superior to prior art in speed, accuracy, objectivity and repeatability; the embodiments of the invention give new life to A-mode breast cancer diagnosis after the entire ultrasound industry had called it "obsolete"; the invention solves non-obvious problems in numerical analysis of digital ultrasound data that were never before even recognized; the invention corrects a serious flaw in the prior art method of A-scan area ratios by removing irrelevant data samples from the calculation.

Although the invention may have been suggested by prior art, that art lacked modern digital devices and digital data processing methods to implement that suggestion in a manner that is convenient, economical, and easy to use. The fact that those skilled in the art have not implemented a digital A-mode ultrasonic system for classifying abnormal breast masses indicates that the invention, taken as a complete integrated system, is not obvious.

Although the description above contains many specifications, these should not be construed as limiting the scope of the invention but as merely providing illustrations of some of the presently preferred embodiments of this invention.

Thus the scope of the invention should be determined by the appended claims and their legal equivalents, rather than by the examples given.

In accordance with embodiments and methods of the invention, an automatic classification of an observed soft tissue mass(es), an example of which is breast mass, is disclosed to detect one of two types of masses—either likely benign or likely malignant—using only the data from a single-element A-mode probe.

In the foregoing embodiments, component 100 is a digital single-element ultrasound probe, contrasted with an analog single-element probe in the prior art. Component 200 is a data processing device, replacing the activities performed by the trained physician 330 in the prior art. In the preferred embodiment of the invention the data processing device is an embedded data processing computer within a smartphone, comprised of a CPU and memory and operating system software. However, the presently disclosed invention is not limited to only such devices.

Within the computer within the data processing device, a stored program 210 takes incoming digital echo vectors from the digital probe 100 and performs data normalization, filtering, noise reduction, and calibration activities—absent in prior analog art, but well known in the current art.

Component 220 uses a well-known numerical analysis techniques, known as the Runge-Kutta method, to compute a digital estimate of the area under an inferred Echograph wave form. The Echograph is not displayed, as it was in prior analog art, but is stored as an ordered array of integers within the data processing device. Component 220 also compares the area under the observed inferred Echograph to the baseline area under previously computed benign masses.

Component 230 is a digital value representing a baseline of areas calculated from known benign masses. This baseline value is stored in the data processing device where it is incorporated into automatic data processing steps. This is unlike the baseline value in the prior art which was stored on paper and used by human manual computing methods.

Component 240 is a display means comprised of a solid color rectangle area with a layer of text on top. Component 240 communicates the inferred classification to the user of the system directly, without having to be communicated orally by a physician intermediary, as was done in the prior art.

Although the present invention has been described in terms of specific embodiments, it is anticipated that alterations and modifications thereof will no doubt become apparent to those skilled in the art. It is therefore intended that the following claims be interpreted as covering all such alterations and modification as fall within the true spirit and scope of the invention.

What is claimed is:

1. A system for classifying palpable breast masses using digital a-mode Echographs, comprising:
    (a) an ultrasound transceiver apparatus, including a probe being a single-element single-vector a-mode probe, a sampling circuit for digitally sampling analog echo values, the ultrasound transceiver apparatus configured to transmit echo data in a form of data vectors to a data processing apparatus,
    (b) the data processing apparatus containing a receiver operative to receive, said data vectors from said ultrasound transceiver probe, a last-in-first-out buffer configured to store the received data vectors until the received data vectors can be processed, the data processing apparatus configured to communicate results of the received data vectors to a user of said system, the data processing apparatus including a stored computer program that upon execution thereof thereby causing processing of the received data vectors comprising the following steps:
        step 1 grabbing the received data vector from said last-in-first-out buffer,
        step 2 transforming the data vector from step 1, so that it is in a form of a one-dimensional array of signed integer values ranging from a maximum negative amplitude value to a maximum positive amplitude value, or
        step 3 transforming the data vector from step 2, by keeping only an upper-side band so that only zero amplitude values and positive integer amplitude values remain,
        step 4 truncating echo amplitude data from the data vector resulting from an ultrasound energy passing through an epidermal layer of the user's body, and replacing the data values with values equal to zero,
        step 5 approximating an a-scan amplitude-time area for the data vector from step 4 by summing all of the digital time-sampled amplitude values from step 4,
        step 6 calculating an a-mode area ratio by dividing the a-scan amplitude-time area by a global constant representing a threshold amplitude-time area for discriminating abnormal masses from non-abnormal masses,
        step 7 deciding on whether an observed mass is likely abnormal or likely non-abnormal, using the following logic: when the a-scan area ratio is greater than 1.0, consider an observed mass to be likely abnormal; otherwise consider the observed mass to be likely not abnormal,
        step 8 communicating the result of step 7 to a system user, using the following logic: when the observed mass is likely abnormal, painting a result text box on a display with a first color and overlaying the first-colored result text box with a first text string; otherwise, painting a result text box on a display with a second color and overlaying the second-colored text box with a second text string, and
        step 9 looping back to step 1 and grabbing the next data vector for processing.

2. The system of claim 1 wherein the probe is a b-mode probe and configured to extract only a central data vector from each b-mode image frame.

3. The system of claim 1 wherein the data processing apparatus is a smartphone.

4. The system of claim 1 wherein the data processing apparatus also is configured to generate audible sounds by making a selection from a plurality of stored digital sound files.

* * * * *